United States Patent [19]

Frazee et al.

[11] Patent Number: 4,863,944
[45] Date of Patent: Sep. 5, 1989

[54] DOPAMINE-β-HYDROXYLASE INHIBITORS

[75] Inventors: James S. Frazee, Collingswood; Carl Kaiser, Haddon Heights, both of N.J.

[73] Assignee: SmithKline Beckman Corporation, Philadelphia, Pa.

[21] Appl. No.: 202,620

[22] Filed: Jun. 6, 1988

Related U.S. Application Data

[62] Division of Ser. No. 723,689, Apr. 16, 1985, Pat. No. 4,772,723, which is a division of Ser. No. 484,125, Apr. 12, 1983, Pat. No. 4,501,741.

[51] Int. Cl.$^4$ ............................................. C07D 233/04
[52] U.S. Cl. ........................................ 514/400; 548/342; 548/343
[58] Field of Search ................ 514/385; 548/342, 343, 548/353

[56] References Cited

U.S. PATENT DOCUMENTS 3,915,980 10/1975 Gebert et al. ..................... 260/309
4,000,079 12/1976 Rasp et al. ......................... 548/353

FOREIGN PATENT DOCUMENTS 615920 2/1980 Fed. Rep. of Germany ........ 233/64
1155580 6/1969 United Kingdom ..................... 49/36

Primary Examiner—Richard L. Raymond
Assistant Examiner—Raymond Covington
Attorney, Agent, or Firm—Stuart R. Suter; Alan D. Lourie

[57] ABSTRACT

Potent DBH Inhibitors having the formula:

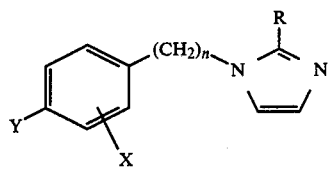

wherein R is —CO$_2$H or —CH$_2$NHR$^1$ can be used to inhibit DBH activity in mammals.

26 Claims, No Drawings

DOPAMINE-β-HYDROXYLASE INHIBITORS

This is a divison of application Ser. No. 723,689 filed Apr. 16, 1985 now U.S. Pat. No. 4,772,723 which is a division of application Ser. No. 484,123 filed Apr. 12, 1983 now U.S. Pat. No. 4,501,471.

FIELD OF THE INVENTION

This invention relates to inhibitors of dopamine-β-hydroxylase.

BACKGROUND OF THE INVENTION

In the catecholamine biosynthetic pathway, tyrosine is converted in three steps to norephinephrine (NE). Intermediates are dihydroxyphenylalanine (DOPA) and dopamine (DA). The latter is hydroxylated to norepinephrine by dopamine-β-hydroxylase (DBH) in the presence of oxygen and ascorbic acid.

Inhibition of catecholamine activity has been found to decrease hypertension. See, for example, Matta et al., Clin. Pharm. Ther. 14, 541 (1973), and Teresawa et al., Japan Circ. J. 35, 339 (1971). Weinshilboum, Mayo Clin. Proc. 55, 39 (1980), reviews compounds which inhibit catecholamine activity by interfering with adrenergic receptors. Alternatively, the catecholamine biosynthetic pathway can be suppressed at any of the three steps, resulting in decreased levels of NE. In addition to decreasing hypertension, inhibitors of NE synthesis are active as diuretics, natriuretics, cardiotonics and vasodilators. Inhibition of DBH activity can have the added advantage of increasing levels of DA, which as reported by Ehrreich et al., "New Antihypertensive Drugs," Spectrum Publishing, 1976, pp. 409–432, has been found to have selective vasodilator activity at certain concentrations.

DBH inhibitors have also been shown to reduce or prevent formation of gastric ulcers in rats by Hidaka et al., "Catecholamine and Stress," edit. by Usdin et al, Permagon Press, Oxford, 1976, pp. 159–165 and by Osumi et al., Japan. J. Pharmacol. 23, 904 (1973).

A number of DBH inhibitors are known. These are generally divided into two classes, namely, metal chelating agents, which bind to copper in the enzyme, and phenethylamine analogues. Rosenberg et al., "Essays in Neurochemistry and Neuropharmacology, Vol. 4," edit. by Youdim et al., John Wiley & Sons, 1980, pp. 179–192, and Goldstein, Pharmacol. Rev. 18(1), 77 (1966), review DBH inhibitors. The former report that many of the potent DBH inhibitors have a hydrophobic side chain of size comparable to the aromatic ring of DA, leading the authors to suggest that incorporation of a terminal hydroxyl group on a 4- to 6-carbon side chain on a phenethylamine analogue might yield a potent inhibitor.

Known inhibitors include:

5-alkylpicolinic acids [See, Suda et al., Chem. Pharm. Bull. 17, 2377 (1969); Umezawa et al., Biochem. Pharmacol. 19, 35 (1969); Hidaka et al., Mol. Pharmacol. 9, 172 (1973); Miyano et al., Chem. Pharm. Bull. 26, 2328 (1978); Miyano et al., Heterocycles 14, 755 (1980); Claxton et al., Eur. J. Pharmacol. 37, 179 (1976)];

BRL 8242 [See, Claxton et al., Eur. J. Pharmacol. 37, 179 (1976)];

1-alkyl-2-mercaptoimidazole [See, Hanlon et al., Life Sci. 12, 417 (1973); Fuller et al., Adv. Enzyme Regul. 15, 267 (1976)];

substituted thioureas [See, Johnson et al., J. Pharmacol. Exp. Ther. 168, 229 (1969)]; and benzyloxyamine and benzylhydrazine [See, Creveling et al., Biochim. Biophys. Acta 64, 125 (1962); Creveling et al., Biochim. Biophys. Res. Commun: 8, 215 (1962); van der Schoot et al., J. Pharmacol. Exp. Ther. 141, 74 (1963); Bloom, Ann. N.Y. Acad. Sci. 107, 878 (1963)].

All of the above compounds except benzyloxyamine and benzylhydrazine apparently owe their inhibitory effect to metal chelating properties. Alkyl derivatives of 2-mercaptoimidazole are more potent, presumably due to non-specific interaction of the alkyl substituent with the enzyme. Benzyloxyamine and benzylhydrazine are phenethylamine derivatives which apparently act as competitive inhibitors.

In addition to the above compounds, Runti et al., Il Farmaco Ed. Sc. 36, 260 (1980), report that other fusaric acid derivatives and analogues can inhibit DBH. These include phenopicolinic acid, which is reported to have twice the inhibitory activity of fusaric acid, and 5-(4-chlorobutyl)picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., Molecular Pharmacology, 9, 172–177 (1972) report that 5-(3,4-dibromo)butyl picolinic acid and 5-(dimethyldithiocarbamoyl)methyl picolinic acid are DBH inhibitors.

Bupicomide, 5-(n-butyl)picolinamide, is reported by Enrreich et al., "New Antihypertensive Drugs," Spectrum Publications, 1976, pg. 409–432, to be a DBH inhibitor and to have antihypertensive activity.

Friedman et al. Psychosomatic Med. 40, 107 (1978), report that patients treated with alpha-methyl-DOPA, guanethidine and reserpine, but not propanolol and diuretics, have lowered DBH levels, although significance of the observation is uncertain.

DBH hydroxylates a variety of phenethylamine substrates. Rosenberg et al., "Essays in Neurochemistry and Neuropharmacology, Vol. 4," edit. by Youdim et al. John Wiley & Sons, 1980, pp. 163–209, extensively review the chemistry of DBH, including, at pp. 176–179 and 196–202, proposed mechanisms of action. There is not yet a known, satisfactory model of the mechanism of action of DBH.

Although there are many known inhibitors of DBH, none of these agents has found clinical application because of non-specific, often toxic, properties they possess. Fusaric acid, for example, has been found to be hepatotoxic. See, for example, Teresawa et al., Japan. Cir. J. 35, 339 (1971) and references cited therein. Presumably, the picolinic acid structure interacts with a number of metalloproteins and enzymes in non-specific fashion to produce observed side effects.

In U.K. specification No. 1,155,580 are disclosed compounds having the formula:

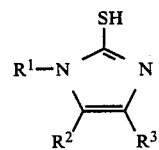

wherein $R^2$ and $R^3$ can be H and $R^1$ can be substituted phenyl. The compounds are said to have analgesic, anti-inflammatory and antipyretic properties. Gebert et al., U.S. Pat. No. 3,915,980, disclose such compounds wherein $R^1$ can be phenyl or phen ($C_{1-3}$) alkyl, as intermediates to imidazolyl-2-thioalkanoic acid esters.

Iverson, *Acta Chem. Scand.* 21, 279 (1967) reports a compound having the formula:

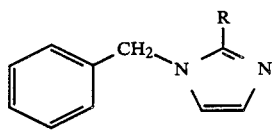

wherein R can be —$CO_2H$ or —$CH_2NHC_6H_5$, but does not report a pharmaceutical use for the compound.

SUMMARY OF THE INVENTION

The invention resides in the discovery that DBH can be inhibited by a compound having an imidazole-2-carboxylic acid or 2-aminomethyl imidazole moiety and a phenethylamine analogue moiety. More particularly, the invention is selected novel compounds having the formula:

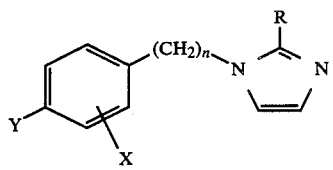

wherein
Y is —H, —OH, —$OCH_3$, —F, —$CF_3$ or $C_{1-4}$ alkyl;
X is —H, —OH, —$OCH_3$, —F, —$CF_3$, $C_{1-4}$ alkyl, or any accessible combination thereof up to four substituents;
R is —$CO_2H$ or —$CH_2NHR^1$;
$R^1$ is —H, phenyl or benzyl; and,
n is 0–4, or a pharmaceutically acceptable acid addition salt or hydrate thereof, provided that when R is —$CO_2H$ or —$CH_2NHC_6H_5$, X is —H and n is 1, Y is not —H.

In one preferred embodiment of the compounds of the invention, R is —$CO_2H$ and n is 1 or 3. In a second such preferred embodiment, R is —$CH_2NHR^1$; Y is —H or —OH; $R^1$ is —H or benzyl; and n is 1.

The invention is also a method of inhibiting DBH activity in mammals which comprises administering internally to a subject an effective amount of a compound having the formula:

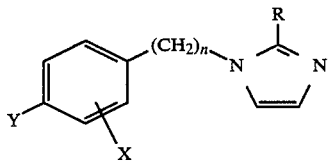

wherein
Y is —H, —OH, —$OCH_3$, —F, —$CF_3$ or $C_{1-4}$ alkyl;
X is —H, —OH, —$OCH_3$, —F, —$CF_3$, $C_{1-4}$ alkyl, or any accessible combination thereof up to four substituents;
R is —$CO_2H$ or —$CH_2NHR^1$;
$R^1$ is —H, phenyl or benzyl; and,
n is 0–4, or a pharmaceutically acceptable acid addition salt or hydrate thereof.

In the preferred method of the invention, R is —$CO_2H$ and n is 1 or 3, or, R is —$CH_2NHR^1$, Y is —H or —OH, $R^1$ is —H or benzyl, and n is 1.

The invention includes pharmaceutical compositions comprising the compounds which are useful in the method of the invention and a pharmaceutical carrier. Pharmaceutically acceptable acid addition salts, and hydrates, are included within the above formulae.

DETAILED DESCRIPTION OF THE INVENTION

The compunds of the invention contain a weak metal-chelating functional group. They also contain a phenyl moiety as do phenethylamine analogue inhibitors such as benzyloxyamine, benzylhydrazine, tryptamine and serotonin.

The compounds of the invention can be prepared from corresponding 2-mercapto-1-(4-methoxyaryl-)imidazoles by procedures such as those illustrated in the Examples below. Starting mercaptoimidazoles are known (see, for example, U.S. Pat. No. 3,915,980 and U.K. Pat. No. 1,155,580) or can be prepared from corresponding benazldehydes, which are known and described in published references or are readily accessible by known techniques, such as illustrated in Scheme I, depicted below, wherein $X^1$ and $Y^1$ are X and Y, respectively, except that when Y is —OH, $Y^1$ is —$OCH_3$ and when X is —OH, $X^1$ is —$OCH_3$. As illustrated, n is one, although n can be 0–4. Scheme I illustrates reductive amination of the benzaldehydes (I) with an aminoacetaldehyde acetal followed by reduction by, for example, catalytic hydrogenation or treatment with a reducing agent such as $NaBH_4$, $LiAlH_4$ or $AlH_3$, to provide intermediate substituted benzylamines (II). Upon reaction with acidic thiocyanate, the intermediates II yield starting mercaptoimidazole compounds (III) which can be converted to the compounds of the invention by procedures known in the art, such as described below and as illustrated in the examples which follow.

Scheme I

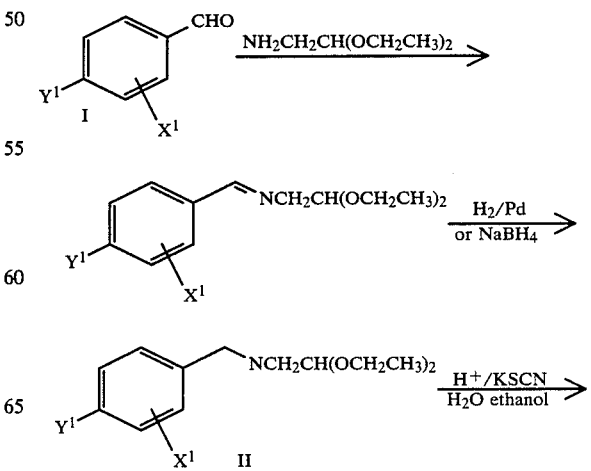

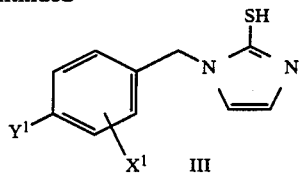

The 1-phenyl substituted 2-mercaptoimidazole starting compounds (n is 0) are preferably prepared by reaction of an appropriately substituted phenyl isothiocyanate with an aminoacetaldehyde acetal followed by strong acid catalyzed cyclization, as illustrated in Example 1, below.

The compounds wherein n is 2, 3 or 4 are preferably prepared as described in Example 4, below. Coupling of substituted phenyl alkanoic acids as the acid chlorides with aminoacetaldehyde acetals and subsequent reduction provides such intermediate substituted phenyl alkylamines.

$Y^1$ in Scheme I is the same as Y except that when Y is —OH, $Y^1$ is —OCH$_3$; deprotection of the 4-alkoxy group with, for example, BBr$_3$ or HBr, or nucleophilic aromatic substitution with dilute hydroxide, provides the phenol (Y is —OH). X may be one or more substituents at the 2-, 3-, 5- or 6-positions provided the combination of substituents is accessible, that is, does not result in significant instability due to steric hindrance. When $X^1$ is —OCH$_3$, it can be deprotected as described above for $Y^1$.

Raney® nickel desulfurization of the starting mercaptoimidazoles (III) provides parent aralkylimidazoles which can be lithiated to provide intermediate aralkyl substituted 2-lithioimidazoles. The lithio-substituent can be replaced such as by quenching with disubstituted formamides to give the 2-aldehydes, as in Example 5, or with CO$_2$ to give the 2-carboxylic acid, as in Example 9.

The corresponding substituted aminomethyl compounds (R is —CH$_2$NHR$^1$ wherein R$^1$ is —H, phenyl or benzyl) can be prepared from the 2-aldehydes by reduction of intermediate 2-aldoximes or o-alkyl ethers of 2-aldoximes as illustrated in Example 6, or by reductive amination with primary or secondary amines as illustrated in Example 7.

The pharmaceutically acceptable acid addition salts of the compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of the invention, because they can be used to inhibit DBH activity, have therapeutic value as diuretic, natriuretic, cardiotonic, antihypertensive and vasodilator agents, as well as antiulcerogenic agents. Compounds of the invention and the compounds wherein R is —CO$_2$H or —CH$_2$NHC$_6$H$_5$, Y is —H, X is —H and n is 1, which compounds are useful in the method of the invention, were screened for in vitro DBH inhibition by a standard procedure for assaying conversion of tyramine to octopamine in the presence of DBH. Octopamine was assayed following sodium periodate oxidation to p-hydroxybenzaldehyde by measuring spectrophotometric absorbance at 330 nm. Results are given in Table I, below. Inhibition is given in molar concentration of compound at which DBH activity was halved (IC$_{50}$). Melting points (mp) are given in °C. Fusaric acid, by this test was found to have an IC$_{50}$ of $8 \times 10^{-7}$.

TABLE I

| | Compound | | | | |
|---|---|---|---|---|---|
| R | Y | X | n | mp | IC$_{50}$ |
| CH$_2$NH$_2$.2HBr | OH | H | 1 | 252–254 | $3.5 \times 10^{-5}$ |
| CO$_2$H.HCl | H | H | 1 | 129 (dec) | $1.1 \times 10^{-5}$ |
| CO$_2$H.HCl | OH | H | 1 | 142 (dec) | $9.0 \times 10^{-5}$ |
| CO$_2$H.¼ H$_2$O | OH | H | 3 | 136 (dec) | $7.0 \times 10^{-5}$ |
| CO$_2$H.HCl | OCH$_3$ | H | 1 | 132 (dec) | $7.5 \times 10^{-5}$ |
| CH$_2$NHC$_6$H$_5$. 2HBr | OH | H | 1 | 198–200 | $>10^{-4}$ |
| CO$_2$H.HCl | OCH$_3$ | H | 3 | 130 (dec) | $9.5 \times 10^{-5}$ |
| CH$_2$NH$_2$.2HCl | H | H | 1 | 185–187 | $2.4 \times 10^{-4}$ |
| CH$_2$NHC$_6$H$_5$.2HCl | H | H | 1 | 206 | $1.0 \times 10^{-4}$ |

The following procedure was used to test, for in vivo activity, compounds which can be used to inhibit DBH activity in mammals, including certain illustrative compounds of the invention. The compounds wherein R is —CO$_2$H or —CH$_2$NHC$_6$H$_5$, X is —H, Y is —H and n is 1 are not compounds of the invention but can be used in the method of the invention.

Male, Okamoto-Aoki strain spontaneously hypertensive rats, aged 16–20 weeks, were used for testing. The afternoon before testing, the animals were fasted and the following morning the first dose of the test compound was administered, p.o., along with a 25 ml/kg load of normal saline. The animals were then placed in metabolism cages, three per cage, and urine was collected for three hours and subsequently analyzed for sodium, potassium, and creatinine. Indirect systolic blood pressure and heart rate were measured via a tail-cuff method and the animals received an identical second does of the test compound. Two hours after the second dose, the systolic blood pressure and heart rate were again determined. Drugs were administered as a solution or suspension in normal saline with 0.02% ascorbic acid.

Three rats weighing 270–320 g were used. Each received two intraperitoneal injections, in a 24 hour period, of a dose volume of 5 mL and a dose concentration of 50 mg/kg or 25 mg/kg, in 0.9% NaCl, following a 24 hour pretreatment dose. Averaged results were as tabulated in Table II, below. Averaged results with control animals, three per experiment, are reported in parentheses below results of test animals.

TABLE II

| Compound and dose | Electrolytes Excreted (μEq/rat) | | Urine Volume (ml/rat) | Na$^+$/K$^+$ ratio | Systolic Blood Pressure (mmHg) | | Heart Rate (beats/min) | |
|---|---|---|---|---|---|---|---|---|
| | Na$^+$ | K$^+$ | | | 1st dose | 2nd dose | 1st dose | 2nd dose |
| Y = OH X = H | 217.36 | 74.27 | 3 | 2.927 | 181 | 175 | 440 | 480 |

TABLE II-continued

| Compound and dose | Electrolytes Excreted (μEq/rat) | | Urine Volume (ml/rat) | Na+/K+ ratio | Systolic Blood Pressure (mmHg) | | Heart Rate (beats/min) | |
|---|---|---|---|---|---|---|---|---|
| | Na+ | K+ | | | 1st dose | 2nd dose | 1st dose | 2nd dose |
| R₁ = CH₂NHR¹ R = C₆H₅.2HBr n = 1 dose = 50 mg/kg | (188.23) | (60.16) | (4) | (3.129) | (172) | (182) | (480) | (480) |
| Y = H X = H R = CO₂H.HCl n = 1 dose = 50 mg/kg | 272.54 | 214.52 | 15 | 1.270 | 211 | 185 | 440 | 480 |
| | (381.56) | (133.79) | (8) | (2.852) | (174) | (170) | (440) | (460) |
| Y = OH X = H R = CO₂H.½H₂O n = 3 dose = 25 mg/kg | 199.74 | 152.18 | 6 | 1.313 | 176 | 173 | 400 | 440 |
| | (188.23) | (60.16) | (4) | (3.129) | (172) | (182) | (480) | (480) |
| Y = OH X = H R = CH₂NH₂.2HBr n = 1 dose = 25 mg/kg | 223.24 | 103.42 | 3 | 2.159 | 161 | 158 | 420 | 440 |
| | (188.23) | (60.16) | (4) | (3.129) | (172) | (182) | (480) | (480) |

Analysis of the above-tabulated results indicates that the compounds inhibit DBH activity as shown by the IC$_{50}$ data and/or by their in vivo natriuretic, diuretic, and antihypertensive and/or cardiotonic activity. For example, the compound in which R is —CO$_2$H, X and Y are —H and n is 1 showed significant in vivo activity as a natriuretic, diuretic, antihypertensive and cardiotonic agent; the compound in which R is —CO$_2$H, Y is —OH, X is —H, and n is 3 showed significant diuretic activity; the compound in which R is —CH$_2$NH$_2$, Y is —OH, X is —H, and n is 1 showed significant antihypertensive activity. The compound in which R is —CH$_2$NHC$_6$H$_5$, Y is —OH, X is —H and n is 1 showed significant cardiotonic activity. Compounds having diuretic activity are known to be useful as antihypertensives.

The compounds can be incorporated into convenient dosage unit forms such as capsules, tablets or injectable preparations. Pharmaceutical carriers which can be employed can be solid or liquid. Solid carriers include, among others, lactose, terra alba, sucrose, talc, gelatin, agar, pectin, acacia, magnesium stearate, and stearic acid. Liquid carriers include, among others, syrup, peanut oil, olive oil and water. Similarly, the carrier or diluent may include any time delay material, such as glyceryl monostearate or glyceryl distearate, alone or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral end products.

Doses of the present compounds in a pharmaceutical dosage unit will be an effective amount, that is, a nontoxic quantity selected from the range of 0.1–1,000 mg/kg of active compound, preferably 10–100 mg/kg. The selected dose is administered to a patient in need of treatment from 1–5 times daily, orally, rectally, by injection or by infusion. Parenteral administration, which uses a low dose is preferred. However, oral administration, at a higher dose, can also be used when safe and convenient for the patient.

The following examples are illustrative of preparation of compounds of the invention (Examples 6–32) or intermediates therefore (Examples 1–5). The starting compounds of Examples 1–4 are commercially available or are prepared by known techniques. The examples are not intended to limit the scope of the invention as defined hereinabove and as claimed below. All temperatures and melting points (mp) are degrees Celsius (°C.).

EXAMPLE 1

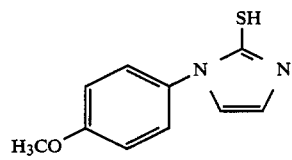

A solution of 10 g (0.06 mole) of p-methoxyphenylisothiocyanate in 100 ml of CHCl$_3$ was treated with 6.3 g (0.06 mole) of aminoacetaldehyde dimethyl acetal. The solvent was evaporated and the residue was recrystallized from ethanol to yield N-(p-methoxyphenyl)-N'-(β,β-dimethoxyethyl)thiourea, 9.2 g (57%). A suspension of this thiourea in a solution of 5 ml of concentrated H$_2$SO$_4$ and 20 ml of H$_2$O was refluxed for 3 hr. The mixture was cooled and a solid was filtered, washed with H$_2$O and dried. Recrystallization from ethanol gave 1-(4-methoxyphenyl)-2-mercaptomidazole, 4.9 g (70%), mp 215°–7°.

The compound is deprotected as illustrated, for example, in Example 6, below, to prepare the phenol (Y is —OH).

EXAMPLE 2

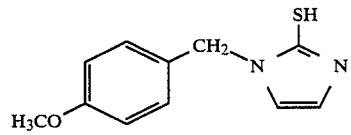

A mixture of 13.6 g (0.1 mole) of anisaldehyde, 13.3 g (0.1 mole) of aminoacetaldehyde diethyl acetal and 1 ml of CH$_3$OH was heated at 95° for 10 minutes. A residue was dissolved in 150 ml of ethanol and hydrogenated over 10% Pd on carbon at 50 psi (0.34 MPa) until H$_2$ uptake was complete. The catalyst was filtered and the filtrate was treated with 10.4 g (0.107 mole) of KSCN, 40 ml of 3N HCl and 40 ml of H$_2$O. The mixture was refluxed, letting the solvent evaporate until the volume of the reaction mixture was 100 ml. After 45 minutes, the mixture was cooled, and a solid was filtered, washed with H$_2$O and dried. Recrystallization from ethanol gave 1-(4-methoxybenzyl)-2-mercaptomidazole, 15.0 g (68%), mp 140°–142°.

EXAMPLE 3

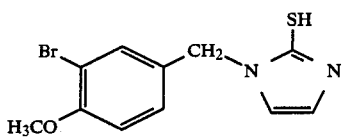

A solution of 10.75 g (0.05 mole) of 3-bromo-4-methoxybenzaldehyde and 6.65 g (0.05 mole) of aminoacetaldehyde diethyl acetal in 25 ml of ethanol was refluxed for 30 minutes. The solvent was evaporated and the residue was dissolved in CH$_2$Cl$_2$. The CH$_2$Cl$_2$ solution of the Schiff base was washed with saturated aqueous NaCl, dried (K$_2$CO$_3$) and filtered, and the solvent was evaporated. Residual Schiff base was dissolved in 100 ml of methanol, cooled to 5°, and treated with 5.0 g of NaBH$_4$. The reaction mixture was allowed to warm to 22° and, after 4 hr, the solvent was evaporated. The residue was taken up in diethyl ether, washed with H$_2$O, dried (MgSO$_4$) and filtered, and the solvent was evaporated. A solution of the residue in CHCl$_3$, upon treatment with ethereal HCl gave, on standing, crystals of N-(3-bromo-4-methoxybenzyl)aminoacetaldehyde diethylacetal hydrochloride, 10.75 g (58%), mp 112°–120°.

A solution of 10.74 g (0.029 mole) of N-(3-bromo-4-methoxybenzyl)aminoacetaldehyde diethyl acetal hydrochloride and 3.37 g (0.35 mole) of KSCN in 50 ml of H$_2$O, 50 ml of ethanol and 5 ml of 3N HCl was refluxed for 4.5 hr. One hundred ml of H$_2$O was added and the mixture was cooled. A solid was filtered, washed with H$_2$O and dried. Recrystallization from ethanol gave 1-(3-bromo-4-methoxybenzyl)-2-mercaptoimidazole, 6.3 g (72%), mp 188°.

EXAMPLE 4

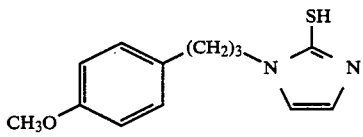

A solution of 12.5 g (0.07 mole) of p-methoxyphenylpropionic acid in 100 ml of CH$_2$Cl$_2$ and one drop of pyridine was treated with 9.8 g (0.077 mole) of oxalyl chloride. After 2.5 hr, the solvents were thoroughly evaporated to give the acid chloride as an oil. A solution of the acid chloride in 100 ml of CH$_2$Cl$_2$ was slowly added to a cold (0°) solution of 14.7 g (0.14 mole) of aminoacetaldehyde dimethyl acetal in 300 ml of CH$_2$Cl$_2$ at a rate such that the temperature stayed below 20°. After 1 hr, the reaction mixture was poured into H$_2$O, and the CH$_2$Cl$_2$ layer was separated and washed with aqueous Na$_2$CO$_3$, 0.5N HCl and H$_2$O. Following drying and evaporation of the solvent, N-(β,β-dimethoxyethyl)-p-methoxyphenylproponamide was left as a solid, 10.3 g (55%). A solution of this amide in 300 ml of diethyl ether was slowly added to a slurry of 4.0 g of LiAlH$_4$ in 400 ml of diethyl ether and 350 ml of tetrahydrofuran (THF). After 3.5 hr at 22°, excess LiAlH$_4$ was cautiously destroyed, the reaction mixture was filtered and the filtrate was evaporated. The residue was dissolved in 100 ml of 0.05N HCl, washed with diethyl ether, basified with NaHCO$_3$ and extracted with diethyl ether. The extracts were dried (MgSO$_4$) and the solvent was evaporated to give N-[3-(4-methoxyphenyl)-propyl]aminoacetaldehyde dimethyl acetal, 4.6 g (52%), as an unstable oil.

A solution of 3.62 g (0.014 mole) of N-[3-(4-methoxyphenyl)propyl]dimethyl acetal and 1.4 g (0.0144 mole) of KSCN in 20 ml of ethanol, 5 ml of H$_2$O and 2 ml of concentrated HCl was refluxed for five hr. Fifty ml of H$_2$O was added, the mixture was cooled and a solid was filtered, washed with H$_2$O and dried. Recrystallization from ethanol gave 1-[3-(4-methoxyphenyl) propyl]-2-mercaptoimidazole, 2.4 g (69%), mp 108°–109°.

EXAMPLE 5

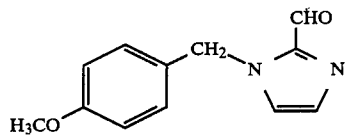

A mixture of 15.0 g (0.068 mole) of 1-(4-methoxybenzyl)-2-mercaptoimidazole and 80 g of Raney ® nickel in 800 ml of ethanol was refluxed for 4 hr. The nickel was filtered off and the filtrate was evaporated. The residue was dissolved in 100 ml of 1N HCl and this solution was washed with diethyl ether. The aqueous layer was basified with NaHCO$_3$ and extracted with ethyl acetate. The extracts were dried (K$_2$CO$_3$) and filtered and the solvent was evaporated, to give 1-(4-methoxybenzyl)imidazole as an oil, 8.7 g (68%). A solution of this oil in acetone was treated with hexamic acid and diethyl ether, and the hexamate salt was crystallized, mp 157°–159°.

A solution of 4.9 g (0.026 mole) of 1-(4-methoxybenzyl)imidazole in a mixture of 150 ml of diethyl ether and 30 ml of tetrahydrofuran (THF) under an atmosphere of argon was cooled to −60° and treated with 18 ml of a 1.7M solution of n-butyl lithium in hexane. After 1.5 hr, 2.25 g (0.031 mole) of dimethylformamide (DMF) was added, and the reaction mixture was warmed to 22°. After 30 min, the reaction mixture was treated with 100 ml of 1.5N HCl, and this aqueous mixture was washed with diethyl ether. The acidic layer was basified with NaHCO$_3$, and extracted with diethyl ether. The extracts were washed well with H$_2$O, dried (K$_2$CO$_3$), and filtered and the solvent was evaporated. The residue was a pale yellow unstable oil, 1-(4-methoxybenzyl)2-formylimidazole, 4.9 g (87%).

EXAMPLE 6

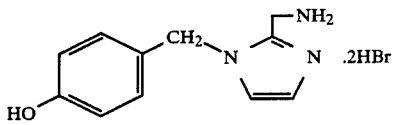

A vigorously stirred suspension of 2.5 g (0.012 mole) of 1-(4-methoxybenzyl)-2-formyl imidazole in 30 ml of $H_2O$ was treated with 6 g of $CH_3CO_2Na.3H_2O$ and 1.5 g of $NH_2OH.HCl$. After 2 hr, the 1-(4-methoxybenzyl)-2-formyl imidazole oxime had solidified. The oxime was filtered, washed with $H_2O$, dried and recrystallized from ethanol to give 1.9 g (68%), mp 201°–204°.

A solution of the oxime in 100 ml of ethanol was hydrogenated over Raney ® nickel at 50 psi (0.34 MPa) for 3 hr. The catalyst was filtered, the filtrate was treated with ethereal HCl and the solvent was evaporated. The residue was recrystallized from ethanol three times to give 1-(4-methoxybenzyl)-2-aminomethyl imidazole dihydrochloride, 0.53 g (22%). A suspension of this salt in 50 ml of $CH_2Cl_2$ was washed with aqueous $NaHCO_3$. The $CH_2Cl_2$ solution of the free base was dried ($K_2CO_3$) and filtered. The filtrate was treated with a solution of 1.0 g (0.004 mole) of $BBr_3$ in 2.5 ml of $CH_2Cl_2$. After 6 hr, methanol was cautiously added and all the solvents were evaporated. The residue was recrystallized from a mixture of methanol and diethyl ether to give 1-(4-hydroxybenzyl)-2-aminomethyl imidazole dihydrobromide, 0.17 g (27%), mp 252°–254°.

EXAMPLE 7

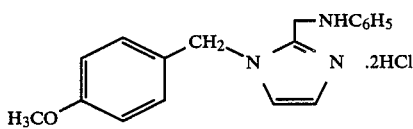

A solution of 1.88 g (0.0087 mole) of 1-(4-methoxybenzyl)-2-formyl imidazole and 0.81 g (0.0087 mole) of aniline in 20 ml of ethanol was refluxed for 1.5 hr. The reaction mixture was cooled to 22° and treated with 3.0 g of $NaBH_4$. After 3 hr, the solvent was evaporated. The residue was taken up in diethyl ether, washed with $H_2O$, dried and filtered and the solvent was evaporated. The residue was converted to its dihydrochloride salt in a mixture of $CH_2Cl_2$ and ethyl acetate with ethereal HCl, to give 1-(4-methoxybenzyl)-2-phenylaminomethyl imidazole dihydrochloride, 1.8 g (56%), mp 146°–157°.

EXAMPLE 8

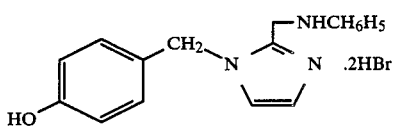

A suspension of 1.6 g (0.0044 mole) of 1-(4-methoxybenzyl)-2-phenylaminomethyl imidazole dihydrochloride in 100 ml of $CH_2Cl_2$ was converted to its free base by washing with aqueous $NaHCO_3$. The $CH_2Cl_2$ was dried ($K_2CO_3$), and filtered, and the filtrate was treated with a solution of 3.3 g (0.013 mole) of $BBr_3$ in 9 ml of $CH_2Cl_2$. After 3 hr, methanol was cautiously added and all the solvents were evaporated. The residue was recrystallized from methanol and diethyl ether to give 1-(4-hydroxybenzyl)-2-phenylaminomethyl imidazole dihydrobromide, 0.73 gm (39%), mp 198°–200°.

EXAMPLE 9

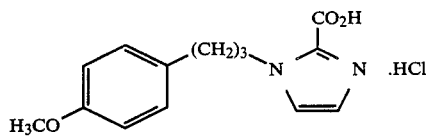

A mixture of 5.0 g (0.02 mole) of 1-[3-(4-methoxyphenyl)propyl]-2-mercaptoimidazole, 40 g of Raney ® nickel and 200 ml of ethanol was refluxed for 4 hr. The Ni was filtered off and the filtrate was evaporated. A residue was dissolved in 25 ml of 1N HCl, and washed with diethyl ether. The aqueous phase was basified with aqueous $NaHCO_3$ and extracted with diethyl ether. The extracts were dried over $K_2CO_3$ and filtered, and the solvent was evaporated. 1-[3-(4-methoxyphenyl)propyl]imidazole remained as an oil, 2.5 g (58%). This oil was dissolved in 100 ml of diethyl ether and cooled to −60° under an argon atmosphere. A 1.7M solution of n-butyl lithium in hexane, 8.2 ml, was added, and the solution was stirred for 1.5 hr. The argon was replaced with dry $CO_2$, and the reaction was stirred vigorously until $CO_2$ uptake ceased. The reaction mixture was warmed to 22°, and the white lithium salt was filtered. The filter cake was washed with diethyl ether, and dissolved in 10 ml of $H_2O$. HCl, 1N, was added to pH4, at which pH a product crystallized. The product was filtered, washed with $H_2O$, and dried. The product was converted to its HCl salt by treatment of an ethanolic solution of the above filtered material with ethereal HCl and diethyl ether. The resultant 1-[3-(4-methoxyphenyl)propyl]imidazole-2-carboxylic acid hydrochloride was 1.2 g (35%), mp 130° (dec).

EXAMPLE 10

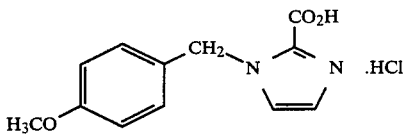

Substantially by the procedure of Example 9, except that the starting mercaptoimidazole was 1-(4-methoxybenzyl)mercaptoimidazole, the compound 1-(4-methoxybenzyl)imidazole-2-carboxylic acid hydrochloride, mp 115° (dec), was prepared.

EXAMPLE 11

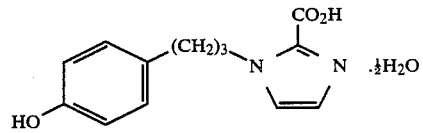

A suspension of 1.1 g (0.0037 mole) of 1-[3-(4-methoxyphenyl)propyl]imidazole-2-carboxylic acid hydrochloride in 100 ml of $CH_2Cl_2$ at 5° was treated with a solution of 2.8 g (0.011 mole) of $BBr_3$ in 7 ml of $CH_2Cl_2$. The mixture was allowed to warm to 22°, and stirred for 5 hr. Methanol was cautiously added, and when a vigorous reaction was over, all solvents were evaporated. A residue was dissolved in 10 ml of H₂O and the pH was adjusted to 3.5 with aqueous NaHCO₃. The product crystallized, was filtered, washed with H₂O and dried. Recrystallization from methanol gave 1-[3-(4-hydroxyphenyl)propyl]imidazole-2-carboxylic acid, hemihydrate, 0.65 g (71%), mp 136° (dec).

EXAMPLE 12

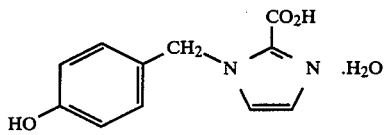

Substantially by the procedure of Example 9, except that the starting mercaptoimidazole was 1-(4-methoxybenzyl)mercaptoimidazole, the compound 1-(4-methoxybenzyl)imidazole-2-carboxylic acid hydrochloride, mp 115°, was prepared. Substantially following the procedure of Example 11, the carboxylic acid was converted to 1-(4-methoxybenzyl)imidazole-2-carboxylic acid hydrochloride hydrate, mp 135°–142° (dec).

EXAMPLE 13

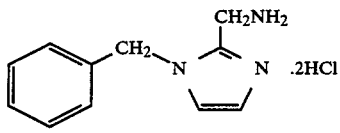

Substantially by the procedure of Example 5, except that the starting mercaptoimidazole was 1-benzyl-2-mercaptoimidazole, a commercially available compound, the compound, 1-benzyl-2-formyl imidazole, was prepared. Substantially following the procedure of Example 6, the benzyl imidazole was converted to 1-benzyl-2-aminomethyl imidazole dihydrochloride, mp 185°–187°.

EXAMPLE 14

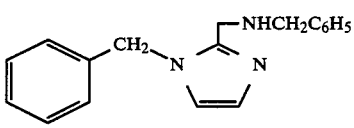

Substantially by the procedure of Example 5, except that the starting mercaptoimidazole was 1-benzyl-2-mercaptoimidazole, a commercially available compound, the compound, 1-benzyl-2-formyl imidazole, was prepared. Substantially following the procedure of Example 7, the benzyl imidazole was converted to 1-benzyl-2-benzylaminomethyl imidazole dihydrochloride, mp 206°.

EXAMPLES 15–23

The illustrative compounds shown in Table III, below, are prepared as the dihydrochloride salts by the procedures of Examples 5, 6, 7 and 8 except that substantially equivalent molar amounts of a corresponding starting mercaptoimidazole and of the other reactants and reagents are used. Except for illustrative compounds in which Y is —OH, the 4-substituent in the aryl moiety of the starting mercaptoimidazole is the same as Y and the deprotection step illustrated in Examples 6 and 8 is omitted. X, R and n are the same in the starting mercaptoimidazoles as in the illustrative compounds. The starting mercapotimidazoles are as follows:

| Example | Mercaptoimidazole |
|---|---|
| 15 | 1-(4'-Fluorobenzyl)-2-mercaptoimidazole |
| 16 | 1-(4'-Trifluoromethylbenzyl)-2-mercaptoimidazole |
| 17 | 1-[3-(3-Methoxy-4-propylphenyl)-propyl)]-2-mercaptoimidazole |
| 18 | 1-[3-(2,4-Dimethyl phenyl)-propyl]-2-mercaptoimidazole |
| 19 | 1-[4-(3,5-Difluoro-4-Methoxy phenyl)-butyl]-2-mercaptoimidazole |
| 20 | 1-(3-Trifluoromethyl-4-fluorophenyl)-2-mercaptoimidazole |
| 21 | 1-(3-Propyl benzyl)-2-mercaptoimidazole |
| 22 | 1-(3,5-Dimethyl-4-trifluoromethyl benzyl)-2-mercaptoimidazole |
| 23 | 1-(2,4,5-Trifluoromethyl)-benzyl)-2-mercaptoimidazole |

The starting mercaptoimidazoles are commercially available or are prepared by known techniques such as those illustrated in preceding Examples. For example, starting 1-phenyl-2-mercaptoimidazoles are prepared by a procedure illustrated by Example 4; starting 2-, 3-, 5- and/or 6-substituted-1-aryl-2-mercaptoimidazoles are prepared by a procedure illustrated by Example 3; starting mercaptoimidazoles for illustrative compounds in which n is 0 are prepared by a procedure illustrated by Example 1.

TABLE III

| | Illustrative Compound | | | |
|---|---|---|---|---|
| Example | X | Y | n | R |
| 15 | H | F | 1 | CH₂NHC₆H₅ |
| 16 | H | CF₃ | 1 | CH₂NHC₆H₅ |
| 17 | 3-OH | (CH₂)₃CH₃ | 2 | CH₂NH₂ |
| 18 | 2-CH₃ | CH₃ | 3 | CH₂NH₂ |
| 19 | 3,5-F₂ | OH | 4 | CH₂NH₂ |
| 20 | 3-CF₃ | F | 0 | CH₂NHCH₂C₆H₅ |
| 21 | 3-(CH₂)₃CH₃ | H | 1 | CH₂NH₂ |
| 22 | 3-CH₃, 5-CH₃ | CF₃ | 1 | CH₂NHC₆H₅ |
| 23 | 2-CF₃ 5-CF₃ | CF₃ | 1 | CH₂NH₂ |

EXAMPLES 24–32

The illustrative compounds shown in Table IV, below, are prepared as the hydrochloride salts by the procedures of Examples 9 and 11 except that substantially equivalent molar amounts of a corresponding starting mercaptoimidazole and of the other reactants and reagents are used. Except for illustrative compounds in which Y is —OH, the 4-substituent in the aryl moiety of the starting mercaptoimidazole is the same as Y and the deprotection step illustrated in Example 11 is omitted. X, R and n are the same in the starting mercaptoimidazoles as in the illustrative compounds.

The starting mercaptoimidazoles are as follows:

| Example | Mercaptoimidazole |
|---|---|
| 24 | 1-(3-Propyl-4-fluorophenyl)-2-mercaptoimidazole |
| 25 | 1-(2-Fluoro-4-trifluoromethyl benzyl)-2-mercaptoimidazole |

-continued

| Example | Mercaptoimidazole |
|---|---|
| 26 | 1-(2-[4-Ethyl phenyl]-ethyl)-2-mercaptoimidazole |
| 27 | 1-(3-[2-Trifluoro-4-methoxy phenyl]-propyl)-2-mercaptoimidazole |
| 28 | 1-(3-[3,4-Dimethoxy phenyl]-propyl)-2-mercatoimidazole |
| 29 | 1-(3-Methoxy-4-trifluoromethyl benzyl)-2-mercaptoimidazole |
| 30 | 1-(3-Methoxy-4-fluorobenzyl)-2-mercaptoimidazole |
| 31 | 1-[3-(2,3-Difluoro phenyl)-propyl]-2-mercaptoimidazole |
| 32 | 1-[2-(2,3,4,5,6-Pentafluoro phenyl)-ethyl]-2-mercaptoimidazole |

The starting mercaptoimidazoles are commercially available or are prepared by known techniques such as those illustrated in preceding Examples. For example, starting 1-phenyl-2-mercaptoimidazoles are prepared by a procedure illustrated by Example 4; starting 2-, 3-, 5- and/or 6-substituted-1-aryl-2-mercaptoimidazoles are prepared by a procedure illustrated by Example 3; starting mercaptoimidazoles for illustrative compounds in which n is 0 are prepared by a procedure illustrated by Example 1.

TABLE IV

| | Illustrative Compound | | | |
|---|---|---|---|---|
| Example | X | Y | n | R |
| 24 | 3-CH$_2$CH$_3$ | F | 0 | CO$_2$H |
| 25 | 2-F | CF$_3$ | 1 | CO$_2$H |
| 26 | H | CH$_2$CH$_3$ | 2 | CO$_2$H |
| 27 | 2-CF$_3$ | OH | 3 | CO$_2$H |
| 28 | 3-OH | OH | 4 | CO$_2$H |
| 29 | 3-OCH$_3$ | CF$_3$ | 1 | CO$_2$H |
| 30 | 3-OCH$_3$ | .F | 1 | CO$_2$H |
| 31 | 2,3-F$_2$ | H | 3 | CO$_2$H |
| 32 | 2,3,5,6-F$_4$ | F | 2 | CO$_2$H |

EXAMPLE 33

The ingredients in Table V, below, are screened, mixed and filled into a hard gelatin capsule.

TABLE V

| Ingredients | Amounts |
|---|---|
| 1-[3-(4-methoxyphenyl)propyl]-imidazole-2-carboxylic acid hydrochloride | 50 mg |
| magnesium stearate | 5 mg |
| lactose | 75 mg |

EXAMPLE 34

The sucrose, calcium sulfate dihydrate and imidazole shown in Table VI, below, are mixed and granulated with a 10% gelatin solution. The wet granules are screened, dried, mixed with the starch talc and stearic acid, screened and comprised into a tablet.

TABLE VI

| Ingredients | Amounts |
|---|---|
| 1-(4-hydroxybenzyl)-2 phenyl-aminomethyl imidazole dihydrobromide | 100 mg |
| calcium sulfate dihydrate | 150 mg |
| sucrose | 20 mg |
| starch | 10 mg |
| talc | 5 mg |

TABLE VI-continued

| Ingredients | Amounts |
|---|---|
| stearic acid | 3 mg |

EXAMPLE 35

1-[3-(4-hydroxyphenyl)propyl]imidazole-2-carboxylic acid hemihydrate, 75 mg, is dissolved in 25 ml of normal saline to prepare an injectable preparation.

While the preferred embodiments of the invention are illustrated by the above, it is to be understood that the invention is not limited to the precise constructions herein disclosed and that the right to all modifications coming within the scope of the following claims is reserved.

We claim:

1. A pharmaceutical composition comprising a compound having the formula:

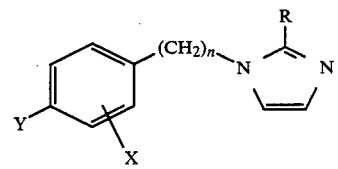

wherein

Y is —H, —OH, —OCH$_3$, —F, —CF$_3$ or C$_{1-4}$ alkyl;

X is —H, —OH, —OCH$_3$, —F, CF$_3$ or C$_{1-4}$ alkyl, or any accessible combination thereof up to four substituents;

R is —CO$_2$H or —CH$_2$NHR$^1$;

R$^1$ is —H, phenyl or benzyl; and, n is 0–4, or a pharmaceutically acceptable acid addition salt or hydrate thereof, and a suitable carrier.

2. The composition of claim 1 wherein R is —CO$_2$H.

3. The composition of claim 1 wherein R is —CH$_2$NHR$^1$.

4. The composition of claim 2 wherein X is —H, Y is —OCH$_3$, —H or —OH and n is 1 or 3.

5. The composition of claim 3 wherein X is —H, Y is —OCH$_3$, —OH or —H, R$^1$ is —H or benzyl and n is 1 or 3.

6. The composition of claim 4 wherein Y is —OCH$_3$ and n is 1.

7. The composition of claim 4 wherein Y is —OCH$_3$ and n is 3.

8. The composition of claim 4 wherein Y is —OH and n is 1.

9. The composition of claim 4 wherein Y is —OH and n is 3.

10. The composition of claim 5 wherein Y is —OH, R$^1$ is —H and n is 1.

11. The composition of claim 5 wherein Y is —OCH$_3$, R$^1$ is benzyl and n is 1.

12. The composition of claim 5 wherein Y is —OH, R$^1$ is benzyl and n is 1.

13. The composition of claim 5 wherein Y is —H, R$^1$ is —H and n is 1.

14. A method for inhibiting DBH activity in mammals which comprises administering internally to a subject an effective amount of a compound having the formula:

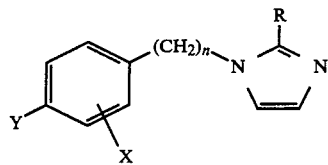

wherein
Y is —H, —OH, —OCH$_3$, —F, —CF$_3$ or C$_{1-4}$ alkyl;
X is —H, —OH, —OCH$_3$, —F, —CF$_3$ or C$_{1-4}$ alkyl, or any accessible combination thereof up to four substituents;
R is —CO$_2$H or —CH$_2$NHR$^1$;
R$^1$ is —H, phenyl or benzyl; and,
n is 0–4 or a pharmaceutically acceptable acid addition salt or hydrate thereof.

15. The method of claim 14 wherein R is —CO$_2$H.
16. The method of claim 14 wherein R is —CH$_2$NHR$^1$.
17. The method of claim 15 wherein X is —H, Y is —OCH$_3$, —OH or —H and n is 1 or 3.
18. The method of claim 16 wherein X is —H, Y is —OCH$_3$, —OH or —H, R$^1$ is —H or benzyl and n is 1 or 3.
19. The method of claim 17 wherein Y is —OCH$_3$ and n is 1.
20. The method of claim 17 wherein Y is —OCH$_3$ and n is 3.
21. The method of claim 17 wherein Y is —OH and n is 1.
22. The method of claim 17 wherein Y is —OH and n is 3.
23. The method of claim 17 wherein Y is —OH, R$^1$ is —H and n is 1.
24. The method of claim 18 wherein Y is —OCH$_3$, R$^1$ is benzyl and n is 1.
25. The method of claim 18 wherein Y is —OH, R$^1$ is benzyl and n is 1.
26. The method of claim 18 wherein Y is —H, R$^1$ is —H and n is 1.

* * * * *